United States Patent [19]

Arndt et al.

[11] Patent Number: 4,754,035

[45] Date of Patent: Jun. 28, 1988

[54] PREPARATION OF 2-ALKYLSULPHONYLALKYLENEPYRIMIDINES

[75] Inventors: Michael Arndt, Wuppertal; Josef Heinrich, Solingen, both of Fed. Rep. of Germany

[73] Assignee: Bayer Aktiengesellschaft, Leverkusen, Fed. Rep. of Germany

[21] Appl. No.: 914,439

[22] Filed: Oct. 2, 1986

[30] Foreign Application Priority Data

Oct. 9, 1985 [DE] Fed. Rep. of Germany ....... 3536065
Dec. 18, 1985 [DE] Fed. Rep. of Germany ....... 3544691
May 15, 1986 [DE] Fed. Rep. of Germany ....... 3616337

[51] Int. Cl.$^4$ .................. C07D 239/32; C07D 239/34; C07D 239/46
[52] U.S. Cl. .................................................. 544/319
[58] Field of Search ........................................ 544/319

[56] References Cited

U.S. PATENT DOCUMENTS 4,234,587 11/1980 Maurer et al. ............... 544/319
4,323,571 4/1982 Maurer et al. ............... 544/319
4,503,057 3/1985 Maurer et al. ............... 544/319

FOREIGN PATENT DOCUMENTS 2838359 3/1980 European Pat. Off. ............. 544/319
2928185 1/1981 European Pat. Off. ............. 544/319
3211035 9/1983 European Pat. Off. ............. 544/319
3324399 1/1985 European Pat. Off. ............. 544/319

Primary Examiner—Richard A. Schwartz
Assistant Examiner—J. Richter
Attorney, Agent, or Firm—Sprung Horn Kramer & Woods

[57] ABSTRACT

A process for the preparation of a 2-alkylsulphonylalkylenepyrimidine optionally substituted in 5- and/or 6-positions of the formula

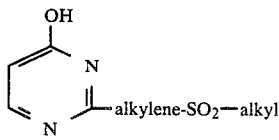

comprising (1) reacting an ammonium halide, alkylmercaptan and chloroalkylenenitrile in the presence of an acid acceptor; (2) mixing an ester with an alkyl acetate in the presence of an alcoholic alcoholate solution and an inert diluent; mixing (1) and (2); after completion of reaction removing the alcohol; adding water and an acid to the residue; optionally concentrating the mixture; and, without further purification and/or isolation, reacting the mixture with hydrogen peroxide at a temperature between approximately $-20°$ C. and $+100°$ C. in the presence of a catalytic amount of a vanadium, tungsten or molybdenum salt, in the presence of water as a diluent.

5 Claims, No Drawings

PREPARATION OF 2-ALKYLSULPHONYLALKYLENEPYRIMIDINES

The invention relates to a new process for the preparation of 2-alkylsulphonylalkylenepyrimidines.

It is known that 2-alkylsulphonylalkylenepyrimidines are obtained if alkylthioalkyleneamidines are reacted with β-keto-esters to give the 2-alkylthioalkylenepyrimidines and the 2-alkylthioalkylenepyrimidines are oxidized, after being worked up and isolated, to give the corresponding sulphonyl derivatives (see, for example, DE-OS (German Published Specifications) Nos. 3,324,399, 3,211,035, 2,928,185 and 2,838,359).

The alkylthioamidines and the β-keto-esters can be prepared by reacting acetonitrile derivatives with ammonium halides and alkylmercaptans or acetic acid ester derivatives with ester derivatives, and, after being worked up and isolated, can be employed as precursors.

The disadvantages in this method of preparation consist in the fact that the 2-alkylsulphonylalkylenepyrimidines are obtained via multi-stage processes, the yields are as a result totally unsatisfactory and a large outlay of energy and time is required for working up and isolating the individual precursors.

It has now been found that 2-alkylsulphonylalkylenepyrimidines of the formula (I)

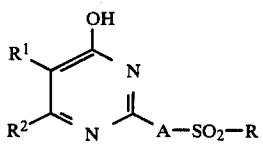  (I)

in which
R represents linear or branched alkyl,
$R^1$ represents hydrogen or optionally substituted radicals belonging to the series comprising alkyl, alkoxy or alkylsulphonyl,
$R^2$ represents hydrogen or optionally substituted alkyl and
A represents linear or branched alkylene,
are obtained if, in order to obtain a reaction mixture (1), (1) ammonium halides of the formula (III)

$$NH_4X \quad (III)$$

in which
X represents halogen,
and alkylmercaptans of the formula (IV)

$$RSH \quad (IV)$$

in which
R has the meaning indicated above,
are added to chloroalkylenenitriles of the formula (II)

$$Cl-A-CN \quad (II)$$

in which
A has the meaning indicated above,
in the presence of acid acceptors and in the presence of diluents, at temperatures between −20° C. and +60° C.; and also, in order to obtain a reaction mixture (2), (2) esters of the formula (VI)

$$R^2-COOR^4 \quad (VI)$$

in which
$R^2$ has the meaning indicated above and
$R^4$ represents alkyl having 1–4 C atoms,
are added to acetic acid esters of the formula (V)

$$R^1-CH_2-COOR^3 \quad (V)$$

in which
$R^1$ has the meaning indicated above and
$R^3$ represents alkyl having 1–4 C atoms,
in the presence of an alcoholate (preferably alkali metal alcoholate) or of an alcoholic alkali metal alcoholate solution, an alcoholic alkali metal alcoholate solution and in the presence of an inert diluent, at a temperature of 0° C. to 40° C.; and the reaction mixture (1) is then added at a temperature of 0° C. to 40° C. to the reaction mixture (2), after the completion of the reaction the alcohol formed is removed, preferably by distillation, where appropriate water and an acid are added to the residue, and the mixture is concentrated and, without further purification and/or isolation, is reacted with hydrogen peroxide at temperatures between −20° C. and +100° C. in the presence of catalytic amounts of a vanadium, tungsten or molybdenum salt, in the presence of water as a diluent.

Surprisingly, the 2-alkylsulphonylalkylenepyrimidines of the general formula (I) can be obtained by the process according to the invention in good yields and in a high state of purity without the isolation of intermediate stages, whereas it would certainly have been expected that the juxtaposition of the above reaction stages without isolating or purifying the intermediate products would not lead to the desired products, or, because of side reactions in individual stages, would lead only to low yields of impure compounds.

It is preferable to prepare, by means of the process according to the invention, the following 2-alkylsulphonylalkylenepyrimidines of the formula (I)

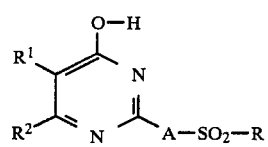  (I)

in which
R represents linear or branched alkyl having 1 to 6 carbon atoms, in particular 1 to 4 carbon atoms,
$R^1$ represents hydrogen or alkyl, alkoxy or alkylsulphonyl, each of which has 1 to 6 carbon atoms, in particular 1 to 4 carbon atoms, and which can optionally be substituted by halogen, $C_1$–$C_2$-alkoxy or $C_1$–$C_2$-alkylsulphonyl,
$R^2$ represents hydrogen or alkyl which has 1 to 6 carbon atoms, in particular 1 to 4 carbon atoms, and which can optionally be substituted by halogen, in particular chlorine or fluorine, $C_1$–$C_2$-alkoxy or $C_1$–$C_2$-alkylsulphonyl, and
A represents linear or branched alkylene having 1 to 6 carbon atoms, in particular 1 to 4 carbon atoms.

If chloroacetonitrile, ammonium chloride and methylmercaptan are used as the starting materials for reaction (1), and if methyl methoxyacetate, methyl formate and a methanolic solution of sodium methoxide are used as the starting materials for reaction (2), and if hydrogen peroxide in the presence of catalytic amounts of ammonium molybdate and water is used as the oxidizing agent, the reaction of the process according to the invention can be outlined by means of the following equation:

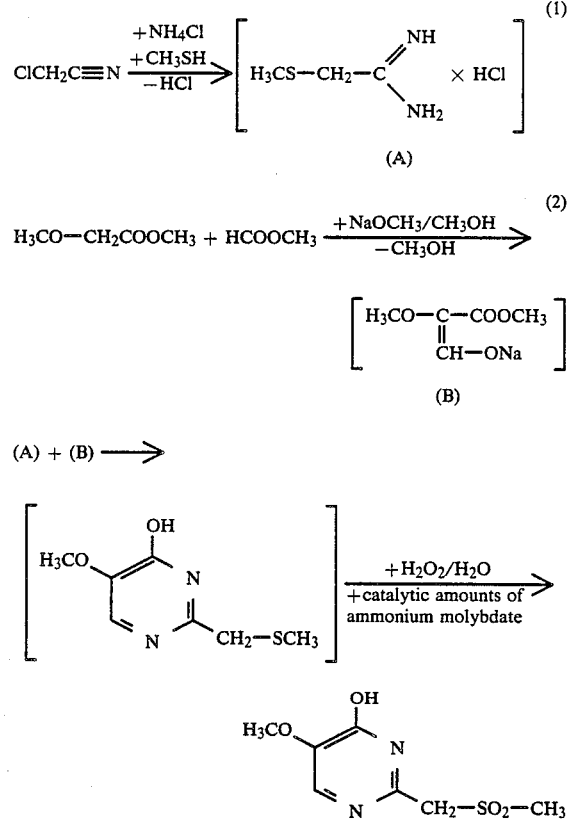

The compounds required as starting materials for carrying out the process according to the invention are defined in a general manner by the formula (II).

In this formula, A represents those radicals which are mentioned above in the definition of the compounds of the formula (I).

The following may be mentioned as examples of the compounds of the formula (II): chloroacetonitrile, 3-chloropropionitrile, 2-chloropropionitrile, 4-chlorobutyronitrile, 2-chlorobutyronitrile and 5-chlorovaleronitrile.

Compounds of the formula (II) are generally known compounds of organic chemistry.

The compounds which are also required as starting materials for the process according to the invention are defined in a general manner by the formulae (III), (IV), (V) and (VI). In these formulae, X, R, $R^1$ and $R^2$ represent the radicals mentioned above in the definition of the compounds of the formula (I). $R^3$ and $R^4$ preferably represent $C_1$-$C_2$-alkyl.

The following may be mentioned as examples of the compounds of the formula (III): ammonium chloride, bromide and iodide.

The following may be mentioned as examples of the compounds of the formula (IV): methyl, ethyl, n-propyl, i-propyl, n-butyl, i-butyl, sec.-butyl and tert.-butyl-mercaptan.

The following may be mentioned as examples of the compounds of the formula (V):

$$R^1—CH_2—COOR^3 \qquad (V)$$

TABLE 1

| $R^1$ | $R^3$ | $R^1$ | $R^3$ |
|---|---|---|---|
| H | $CH_3$ | H | $C_2H_5$ |
| $CH_3$ | $CH_3$ | $CH_3$ | $C_2H_5$ |
| $OCH_3$ | $CH_3$ | $OCH_3$ | $C_2H_5$ |
| $C_2H_5$ | $CH_3$ | $C_2H_5$ | $C_2H_5$ |
| $OC_2H_5$ | $CH_3$ | $OC_2H_5$ | $C_2H_5$ |
| $C_3H_7$ | $CH_3$ | $C_3H_7$ | $C_2H_5$ |
| $OC_3H_7$ | $CH_3$ | $OC_3H_7$ | $C_2H_5$ |
| $C_3H_7$-i | $CH_3$ | $C_3H_7$-i | $C_2H_5$ |
| $OC_3H_7$-i | $CH_3$ | $OC_3H_7$-i | $C_2H_5$ |
| $SCH_3$ | $CH_3$ | $SCH_3$ | $C_2H_5$ |
| $SC_2H_5$ | $CH_3$ | $SC_2H_5$ | $C_2H_5$ |

The following may be mentioned as examples of the compounds of the formula (VI): methyl formate, ethyl formate, methyl acetate and ethyl acetate.

The compounds of the formulae (III), (IV), (V) and (VI) are generally known compounds of organic chemistry.

Diluents are used for the preparation of the reaction mixture (1). Suitable diluents are solvents which are inert under the reaction conditions. These include, in particular, alcohols, such as methanol, ethanol and n-propanol. It is preferable to employ methanol as the solvent.

Acid acceptors are also used for the preparation of the reaction mixture (1). Suitable acid acceptors are preferably alkali metal alcoholates. It is preferable to employ sodium methylate or ethylate as the acid acceptor. The diluent employed is methanol if sodium methylate is employed, and ethanol if sodium ethylate is employed.

The preparation of the reaction mixture (1) is generally effected at temperatures between $-20°$ C. and $+30°$ C., preferably between $-10°$ C. and $+20°$ C. The preparation of the reaction mixture (1) is preferably effected in an inert gas atmosphere. A suitable inert gas is preferably argon or nitrogen. The reaction is preferably carried out in the presence of nitrogen. The reaction mixture (1) is preferably prepared under normal pressure.

In the preparation of the reaction mixture (1), it is preferable to employ, for 1 mol of nitrile of the formula (II), 1.01 to 1.25 mols preferably 1.05 to 1.20 mols of acid acceptor, 1 to 2.00, preferably 1 to 1.5, mols of ammonium halide of the formula (III) and 1 to 1.25 mols, preferably 1 to 1.10 mols, of alkylmercaptan of the formula (IV).

Inert diluents are used for the preparation of the reaction mixture (2). These include, in particular, aromatic hydrocarbons, such as benzene, xylene and toluene, and ethers, such as methyl tert.-butyl ether, diethyl ether and dibutyl ether. It is particularly preferable to employ xylene as the diluent.

Either a solid alcoholate and/or an alcoholic alkali metal solution is used for the preparation of the reaction mixture (2). Alkali metal alcoholates, such as sodium methylate and ethylate, have proved particularly suitable. If an alcoholic alcoholate solution is used, the alcohol employed when sodium methylate is used is methanol, and the alcohol employed when sodium ethylate is used, is ethanol.

The preparation of the reaction mixture (2) is generally effected at temperatures between $0°$ C. and $40°$ C. The range between $0°$ C. and $20°$C. is preferred. The reaction mixture (2) is preferably prepared under normal pressure.

In the preparation of the reaction mixture (2), 1 to 3 mols, preferably 1.0 to 2.2 mols, of ester of the formula (VI) and 1 to 5 mols, preferably 1.3 to 4.2 mols, of alkali metal alcoholate are employed for 1 mol of the compound of the formula (V). The alcoholic solution of alkali metal alcoholate contains 0.5 to 2.5 mols, preferably 0.8 to 2 mols, of alcohol for 1 mol of alkali metal alcoholate.

The acids employed for the process according to the invention are preferably mineral acids such as, for example, hydrochloric acid, sulphuric acid, and phosphoric acid, and acetic acid.

Catalysts suitable for the process according to the invention are preferably molybdenum salts, such as, for example, ammonium molybdate.

The process according to the invention is generally carried out at temperatures between $-20°$ C. and $+100°$ C.; the temperature range between $0°$ C. and $80°$ C., in particular between $20°$ C. and $60°$ C., is preferred. The reactions are generally carried out under normal pressure.

To carry out the process according to the invention the mixtures obtained from about 1 mol of the starting components of formulae (II), (III) and (IV) (reaction mixture (1)) and of formulae (V) and (VI) (reaction mixture (2)) about 1 mol of the oxidizing agent hydrogen peroxide is added.

An oxidizing solution can be prepared for example as follows: to a mixture of 0.01 to 5.0 g (preferably 0.05 to 3.0 g) of a catalyst and 20 to 700 ml, preferably 50 to 500 ml of water, 1.8 to 4.5 mols, preferably 1.9 to 3.5 mols of hydrogen peroxide are added dropwise optionally under cooling. When the reaction is over the resulting product is worked up in a customary manner, that is to say, for example, the resulting precipitate is filtered off with suction, washed dnd dried.

As a rule the compounds of the formula (I) are obtained in a solid form and can be purified by recrystallization. The melting point serves to characterize them.

The 2-alkylsulphonylalkylenepyrimidines prepared by the process according to the invention are used as intermediate products for highly effective insecticides (see DE-OS (German Published Specifications) Nos. 2,838,359, 2,928,185 and 3,211,035).

PREPARATION EXAMPLE

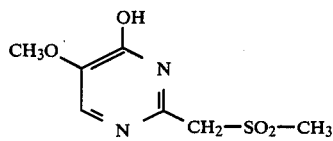

8.4 kg (112 mols) of chloroacetonitrile, followed by 6.5 kg (123 mols) of ammonium chloride, are added, under nitrogen and at $0°$–$5°$ C., to a solution of 0.3 kg (5.5 mols) of sodium methylate in 7.3 kg (228 mols) of methanol. 24 kg of 25% strength methanolic sodium methylate solution and 5.6 kg (117 mols) of methylmercaptan are added at the same temperature. This reaction mixture is added at $20°$ C. to a reaction mixture consisting of 21 kg (388 mols) of sodium methylate, 22 kg (688 mols) of methanol, 24 kg of xylene, 10.4 kg (100 mols) of methyl methoxyacetate and 7.2 kg (120 mols) of methyl formate, which has previously been stirred for 3 hours at $20°$ C. The resulting reaction mixture is stirred for a further 2 hours at $20°$ C., and 30 kg of water are added. The pH is then adjusted to 4.5–5.0 with concentrated hydrochloric acid. The reaction mixture is the concentrated in vacuo (to approx. 5 l) and 0.2 kg of ammonium molybdate is added. 34 kg (300 mols) of 30% strength hydrogen peroxide are then added at a temperature of $40°$ to $45°$ C. and stirring is continued for 30 minutes at $40°$ to $45°$ C. and for 30 minutes at $5°$ C. The precipitated product is filtered off, rinsed with cold water and dried. 17.7 kg (66% of theory) of 4-hydroxy-5-methoxy-2-methylsulphonylmethylpyrimidine of melting point $230°$ C. are obtained in this manner.

It is understood that the specification and examples are illustrative but not limitative of the present invention and that other embodiments within the spirit and scope of the invention will suggest themselves to those skilled in the art.

We claim:

1. A process for the preparation of a 2-alkylsulphonyl-alkylenepyrimidine of the formula

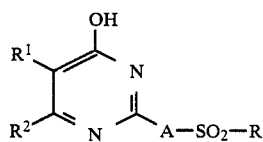

in which
R is linear or branched alkyl,
$R^1$ is hydrogen or optionally substituted alkyl, alkoxy or alkylsulphonyl,
$R^2$ is hydrogen or optionally substituted alkyl, and
A is alkylene,
comprising forming a reaction mixture (1) by mixing an ammonium halide of the formula $NH_4X$ in which
X is halogen,
an alkylmercaptan of the formula

RSH and a chloroalkylenenitrile of the formula

Cl—A—CN in the presence of an acid acceptor and in the presence of a diluent at a temperature between $-20°$ C. and $+60°$ C.; forming a reaction mixture (2) by mixing an ester of the formula $R^2$—COOR$^4$ in which
$R^4$ is alkyl having 1–4 C atoms,
with an acetic acid ester of the formula $R^1$—CH$_2$-COOR$^3$ in which $R^3$ is alkyl having 1–4 C atoms,
in the presence of an alcoholic alcoholate solution and in the presence of an inert diluent, at a temperature of approximately $0°$ C. to $40°$ C.; mixing the reaction mixture (1) at a temperature of approximately $0°$ C. to $40°$ C. with the reaction mixture (2); after completion of reaction removing the alcohol; adding water and an acid to the residue; optionally concentrating the mixture; and, without further purification or isolation, reacting the mixture with hydrogen peroxide at a temperature between approximately −20° C. and +100° C. in the presence of a catalytic amount of a vanadium, tungsten or molybdenum salt, in the presence of water as a diluent.

2. A process according to claim 1, in which
R is alkyl having 1 to 6 carbon atoms,
$R^1$ is hydrogen or alkyl, alkoxy or alkylsulphonyl each of which has 1 to 6 carbon atoms and which can optionally be substituted by halogen, $C_1$-$C_2$-alkoxy or $C_1$-$C_2$-alkylsulphonyl,
$R^2$ is hydrogen or alkyl which has 1 to 6 carbon atoms and which can optionally be substituted by halogen, $C_1$-$C_2$-alkoxy or $C_1$-$C_2$-alkylsulphonyl, and
A is alkylene having 1 to 6 carbon atoms.

3. A process according to claim 1, in which
R is alkyl having 1 to 4 carbon atoms,
$R^1$ is hydrogen or alkyl, alkoxy or alkylsulphonyl, each of which has 1 to 4 carbon atoms and which can optionally be substituted by halogen, $C_1$-$C_2$-alkoxy or $C_1$-$C_2$-alkylsulphonyl,
$R^2$ is hydrogen or alkyl which has 1 to 4 carton atoms and which can optionally by substituted by chlorine or fluorine, $C_1$-$C_2$-alkoxy or $C_1$-$C_2$-alkylsulphonyl, and
X is alkylene having 1 to 4 carbon atoms.

4. A process according to claim 1, wherein the 2-alkylsulphonyl-alkylenepyrimidine is the compound of the formula

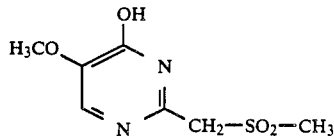

5. A process according to claim 4, wherein the reaction mixture (1) is obtained by reacting chloroacetonitrile with ammonium chloride and methylmercaptan in the presence of sodium methylate and in the presence of methanol, reaction mixture (2) is obtained by reacting a methoxyacetic acid ester with a formic acid ester in the presence of a methanolic methylate solution and in the presence of an aromatic hydrocarbon, after reaction mixture (1) is mixed with reaction mixture (2) water is added and the pH is adjusted to 4,5–5.0 with acid, and the mixture is then concentrated and reacted with hydrogen peroxide in the presence of a molybdate.

* * * * *